(12) United States Patent
Salemi et al.

(10) Patent No.: US 8,197,520 B2
(45) Date of Patent: Jun. 12, 2012

(54) BONE LOSS PLATE

(76) Inventors: Anthony A. Salemi, Bedford, NH (US); Glenn S. Lieberman, Gilford, NH (US)

( * ) Notice: Subject to any disclaimer, the term of this patent is extended or adjusted under 35 U.S.C. 154(b) by 771 days.

(21) Appl. No.: 11/972,828

(22) Filed: Jan. 11, 2008

(65) Prior Publication Data

US 2008/0172095 A1    Jul. 17, 2008

Related U.S. Application Data

(60) Provisional application No. 60/879,896, filed on Jan. 11, 2007.

(51) Int. Cl.
*A61B 17/80* (2006.01)
(52) U.S. Cl. ........................................................ 606/280
(58) Field of Classification Search .......... 606/246–249, 606/280, 285–286; 623/17.11–17.15
See application file for complete search history.

(56) References Cited

U.S. PATENT DOCUMENTS

| | | | |
|---|---|---|---|
| 3,710,789 A | 1/1973 | Ersek | |
| 4,938,768 A | 7/1990 | Wu | |
| 5,211,664 A * | 5/1993 | Tepic et al. | 623/16.11 |
| 5,468,242 A | 11/1995 | Reisberg | |
| 5,487,741 A | 1/1996 | Maruyama et al. | |
| 5,968,098 A | 10/1999 | Winslow | |
| 6,039,762 A * | 3/2000 | McKay | 623/17.11 |
| 6,066,175 A * | 5/2000 | Henderson et al. | 623/17.11 |
| 6,342,055 B1 * | 1/2002 | Eisermann et al. | 623/17.16 |
| 6,443,989 B1 * | 9/2002 | Jackson | 623/17.15 |
| 6,491,724 B1 * | 12/2002 | Ferree | 623/17.11 |
| 6,827,743 B2 * | 12/2004 | Eisermann et al. | 623/23.54 |
| 7,014,659 B2 * | 3/2006 | Boyer et al. | 623/17.15 |
| 7,320,708 B1 * | 1/2008 | Bernstein | 623/17.15 |
| 7,354,452 B2 * | 4/2008 | Foley | 623/17.11 |
| 7,537,616 B1 * | 5/2009 | Branch et al. | 623/17.16 |
| 2004/0181283 A1 * | 9/2004 | Boyer et al. | 623/17.11 |
| 2004/0249377 A1 * | 12/2004 | Kaes et al. | 606/61 |
| 2005/0071008 A1 * | 3/2005 | Kirschman | 623/17.11 |
| 2005/0085913 A1 * | 4/2005 | Fraser et al. | 623/17.11 |
| 2006/0195100 A1 * | 8/2006 | Kirschman | 606/69 |

FOREIGN PATENT DOCUMENTS

WO    WO 03/005938    *    1/2003

* cited by examiner

*Primary Examiner* — Thomas C. Barrett
*Assistant Examiner* — Melissa A Golob
(74) *Attorney, Agent, or Firm* — Robert R Deleault, Esq; Mesmer & Deleault, PLLC

(57) ABSTRACT

A bone loss plate for the rigid fixation of a bone having a bone gap where portions of the bone are absent, the plate includes an elongated fixation plate having a first plate side, a second plate side, a proximal portion, a distal portion, and a middle portion and a tubularly-shaped containment cage connected to the second plate side of the elongated fixation plate, the tubular containment cage having a length shorter than the elongated fixation plate.

3 Claims, 4 Drawing Sheets

BONE LOSS PLATE

This application claims the benefit of U.S. Provisional Patent Application No. 60/879,896, filed Jan. 11, 2007.

BACKGROUND OF THE INVENTION

1. Field of the Invention

The present invention relates generally to medical implants. Particularly, the present invention relates to fracture plates and cages. More particularly, the present invention relates to a bone loss plate for the rigid fixation of long bone fracture where there is significant bone loss at the fracture site or bone loss gaps caused by pathological processes.

2. Description of the Prior Art

Fracture plates and cages have been in use for years. Typically, fracture plates and cages are comprised of separate fracture plates and metallic mesh cages. Plates are used to immobilize bone fractures and to maintain alignment during the healing process. Cages have been used to make up the space in areas of bone loss due to fracture or other pathologic processes.

The main problem with conventional fracture plates is that plates cannot close gaps between the fractured ends of severely damaged bones. Bone does not heal if significant gaps exist between fracture fragments of broken or otherwise damaged opposing bone ends. If there is bone loss at the fracture site the use of a conventional plating system requires the fracture ends to be pulled together shortening the overall length of the original bone.

Alternatively, mesh cylindrical cages filled with osteogenic material may be inserted into the gap prior to assembling the plate system to the fractured bone. A drawback of conventional cages used to fill gaps in damaged bone is that the cages may migrate out of position. Additionally, conventional cages do not provide immobilization of the fractured bone nor can they maintain alignment of the fractured bone.

While these devices may be suitable in some circumstances, they are not as suitable for the rigid fixation of long bone fracture where there is significant bone loss at the fracture site or bone loss gap caused by pathological processes.

U.S. Pat. No. 4,938,768 discloses a bone gap bridging and fusing device. The bone gap bridging device includes first and second pin members adapted to be placed in axial openings formed in the opposed remaining bone portions. Each pin member includes a head and the heads of the pin members interengage one another to prevent relative rotation between the pin members. A collar telescopes over the interengaged heads to lock the pin members axially relative to one another.

This device suffers the disadvantage that tapered openings in axial alignment must be formed in the ends of the bone portions in order to receive the pin members of the device. Additionally, the collar and the pin members must have mating threads as well as set screws to fix the collar in position relative to the pin members, which adds to the cost of the device.

Therefore, what is needed is a device and method to rigidly fix a long bone fracture where there is significant bone loss at the fracture site or caused by pathological processes. What is also needed is a device and method that also fills the gap produced by the bone loss so that shortening does not occur. What is further needed is a device and method that provides immobilization and maintenance of alignment of a bone fracture while eliminating or minimizing the shortening of the bone caused by bone loss.

SUMMARY OF THE INVENTION

It is an object of the present invention to provide a device and method that rigidly fixes a long bone fracture where there is significant bone loss at the fracture site. It is another object of the present invention to provide a device and method that fills the gap produced by the bone loss so that shortening does not occur. It is a further object of the present invention to provide a device and method that provides immobilization and maintains alignment of a bone fracture while eliminating or minimizing the shortening of the bone caused by bone loss. It is still another object of the present invention to provide a device and method that combines cages designed to fit into the areas of bone loss due to severe trauma with a stability providing plate. It is yet another object of the present invention to provide a device and method that eliminates the possibility that the cage will migrate out of optimum position. It is another object of the present invention to provide a weight-bearing surface upon which the fracture ends can be seated during the healing process. It is a further object of the present invention to provide a device that has a known volume. It is an object of the present invention to provide a device that physically contains the osteogenic material placed inside it. It is still another object of the present invention to provide a device that that can fill gaps in long bones produced by pathological processes such as infections, trauma and tumors. It is yet another object of the present invention to provide a device that immobilizes the spine while filling the defects in vertebral bodies or disc spaces.

The present invention achieves these and other objectives by providing a bone loss plate having a fixation plate and a tubularly-shaped containment cage connected to the fixation plate. The fixation plate has a first plate side, a second plate side, is preferably rectangularly shaped, and has a proximal portion, a distal portion and a middle portion. The proximal and distal portions have a plurality of openings through which fasteners are positioned to fixedly attach the plate to the respective ends of the fractured bone.

The tubularly-shaped containment cage is preferably an elliptically-shaped metallic mesh basket that has a diameter approximately equal to the diameter of the fractured bone ends. The plate side of the tubularly-shaped cage is connected to the middle portion of the plate and may optionally be integrally formed into the middle portion of the plate. The tubularly-shaped cage may optionally include cage braces and, preferably, top and bottom cage braces. In the elliptically-shaped embodiment, the top and bottom cage braces are symmetrically placed along a chord line at each end.

Preferably, the tubular containment cage has a shape defined by the shape of the bone to which the bone loss plate is to be attached. Thus, the tubular containment cage is preferably customized for the installed location. It is also preferable that the ends of the tubular containment cage have a diameter about the same as the diameter of the ends of the bones to be joined. The tubular containment cage may optionally be configured to be expandable.

DETAILED DESCRIPTION OF THE PREFERRED EMBODIMENT

Figure 1:
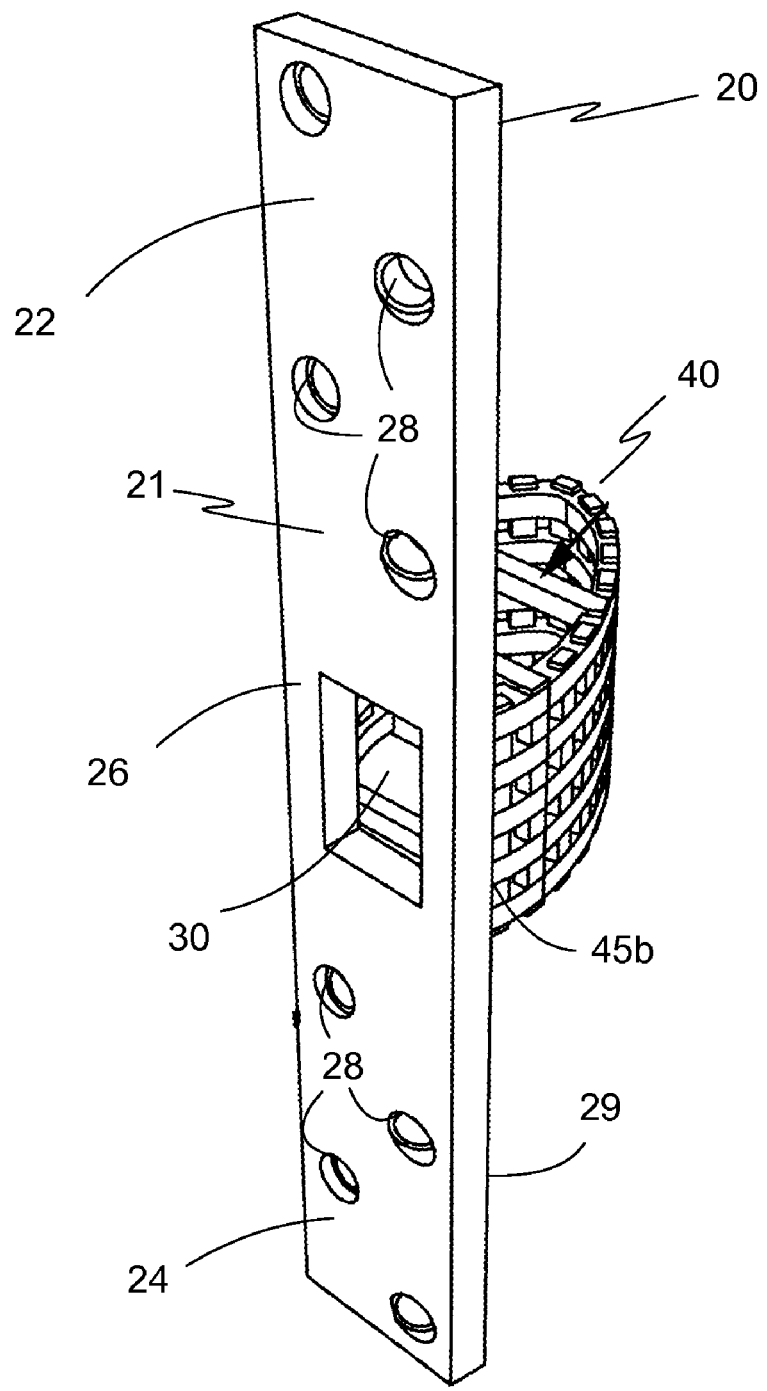
FIG. 1 is a perspective rear view of one embodiment of the present invention showing the bone loss plate.

The preferred embodiment of the present invention is illustrated in FIGS. 1-4. FIG. 1 shows a perspective back view of the bone loss plate 10 of the present invention. Bone loss plate 10 has a fixation plate 20 showing a second plate side 21 and a tubularly-shaped containment cage 40. Fixation plate 20 has a proximal portion 22, a distal portion 24 and a middle portion 26. Proximal portion 22 and distal portion 24 have a plurality of fastener openings 28. Middle portion optionally includes a cage aperture 30 and provides access to the inside of tubularly-shaped containment cage 40.

For example, to treat a tibial fracture in an average adult male, proximal and distal portions 22, 24 of plate 20 are typically about 4 mm. thick, about 20 mm. wide and about 40 mm. long. The plurality of fastener openings 28 in proximal and distal portions 22, 24 also have four or more holes approximately 4 mm. in diameter through which fasteners such as, for example, screws are used to fixedly attach plate 20 to the respective fractured bone ends. The plurality of fastener openings 28 are aligned adjacent the longitudinal axis of plate 20. Fasteners other than screws may be used to fixedly attach plate 20 to the bone. In certain clinical situations, it may be advantageous to form plate ends 32 in a curvilinear shape. In other embodiments, optional cage aperture 30 may be incorporated into the middle section 26 of plate 20 so that osteogenic material can be disposed inside tubularly-shaped cage 40 after positioning bone loss plate 10 in the bone fracture area. It should be understood that osteogenic material can also be disposed inside tubularly-shaped cage 40 before positioning bone loss plate 10 in the bone fracture area.

Figure 2:
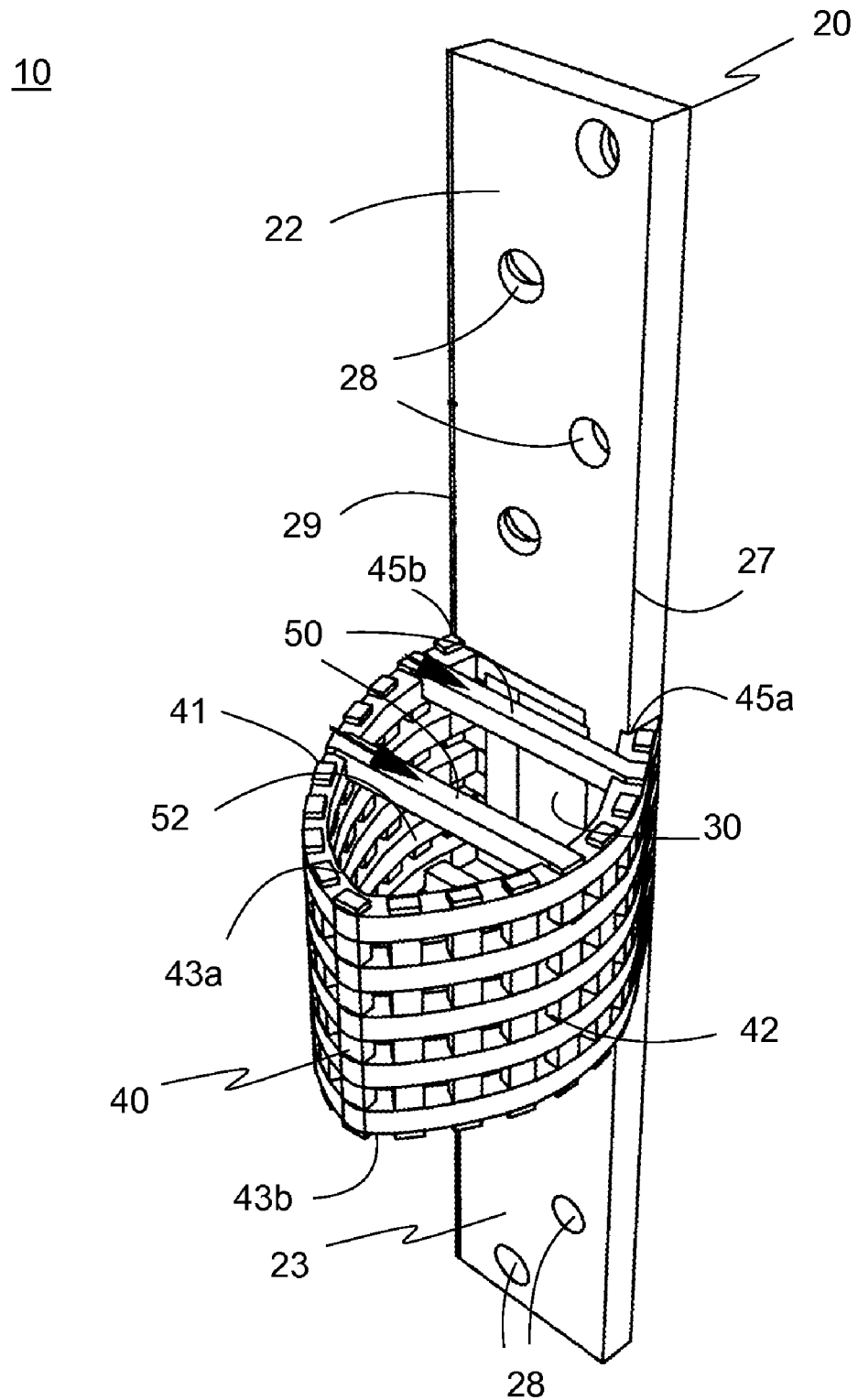
FIG. 2 is a perspective front view of the embodiment in FIG. 1 showing the tubularly-shaped containment cage.
Figure 3:
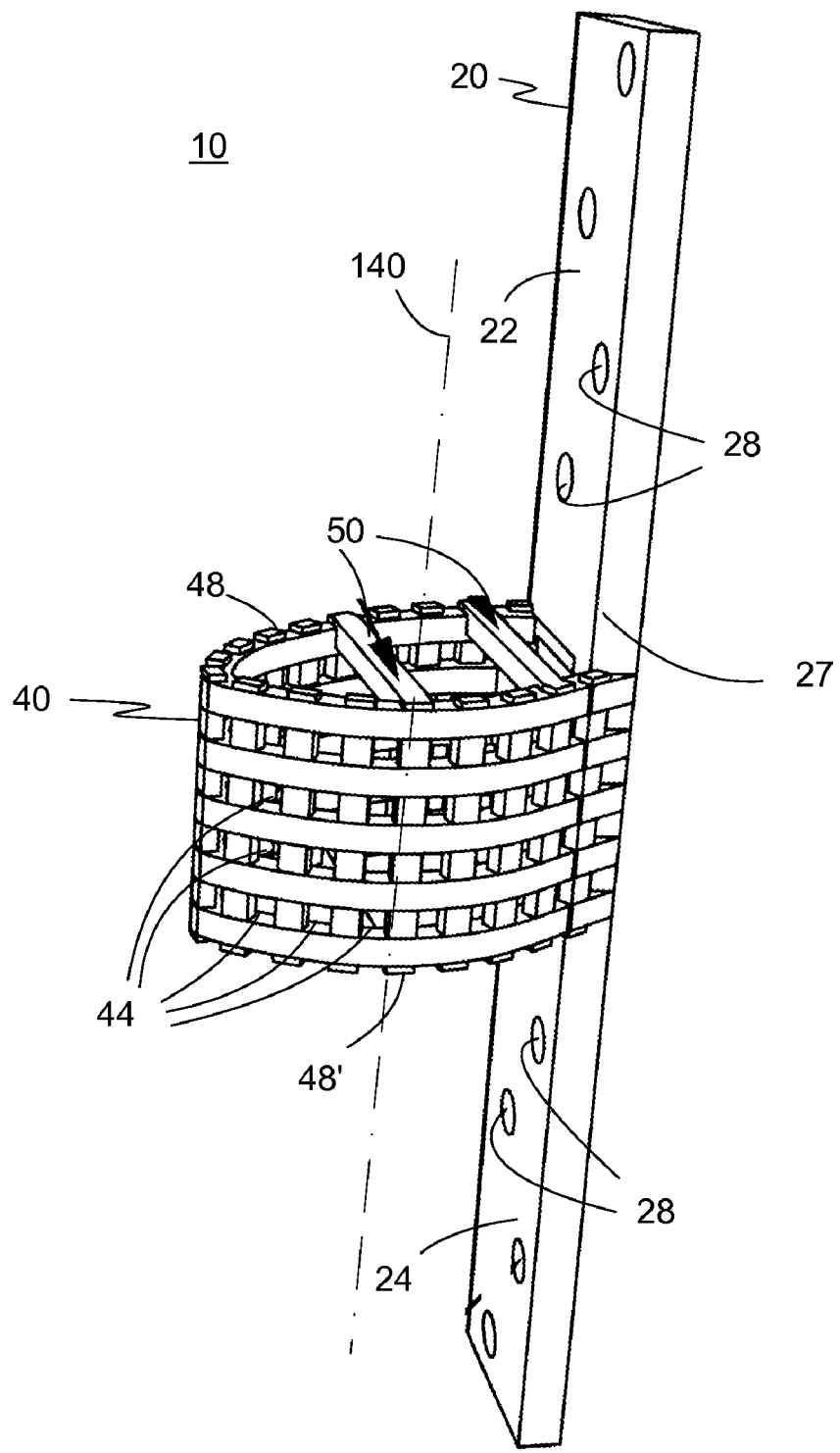
FIG. 3 is a perspective side view of the embodiment in FIG. 1 showing the mesh structure of the tubularly-shaped containment cage.

Turning now to FIG. 2, there is illustrated a perspective front view of the present invention. Tubularly-shaped containment cage 40 is preferably an elliptically-shaped metallic mesh structure 42 that has a diameter approximately equal to the diameter of the fractured bone ends. The plate side of the tubularly-shaped containment cage 40 is connected to middle portion 26 of a first plate side 23 of plate 20 and may optionally be integrally formed into middle portion 26. Containment cage 40 has a circumferential cage wall 41 that defines a cage volume 52 where the circumferential cage wall 41 has a first cage wall end 45a and a second cage wall end 45b. First cage wall end 45a is connected to and extends from a first longitudinal edge 27 of the middle portion 26 of the elongated fixation plate 20 and extends away from the second plate side 22 of the elongated fixation plate 20. Second cage wall end 45b is connected to and extends from a second longitudinal edge 29 of the middle portion 26 of the elongated fixation plate 20. Circumferential cage wall 41 forms a pair of opposed open cage ends 43a, 43b and has a length shorter than the elongated fixation plate 20. Circumferential cage wall 41 also includes a plurality of cage openings 44 disposed throughout circumferential cage wall 41. Tubularly-shaped containment cage 40 may optionally include one or more cage braces 50 and, preferably, top and bottom cage braces 50. In the elliptically-shaped embodiment, the top and bottom cage braces 50 are symmetrically placed along a chord line of tubularly-shaped containment cage 40.

Preferably, tubularly-shaped containment cage 40 is an elliptically-shaped, metallic, mesh cage that is integrally connected to middle portion 26 of plate 20. The mesh structure 42 provides a plurality of cage wall openings 44 and is more clearly shown in FIG. 3. The height of containment cage 40 is dictated by the length of bone that it is intended to replace. The shape of containment cage 40 is dictated by the shape of the bone requiring treatment. Thus, the shape and size of tubularly-shaped containment cage 40 is customized accordingly.

The cross-sectional shape of each end 48, 48' of the tubularly-shaped containment cage 40 is preferably an approximate mirror image of the cross-section of the respective ends of the bone that it is supporting. Containment cage 40 preferably has cage braces 50 symmetrically placed along a chord line at each end 48, 48' and preferably made of the same material as containment cage 40. An optional feature of containment cage 40 is that it may be detachable from fixation plate 20, a feature that would be advantageous in certain instances. In other embodiments, it is advantageous to make containment cage 40 from a material different from that of plate 20. Containment cage 40 may optionally be expandable along its longitudinal axis 140. This optional feature provides a single bone loss plate 20 that is usable in situations where the bone gap varies or is adaptable for different sized bone gaps. This optional feature reduces cost by standardization.

Figure 4:
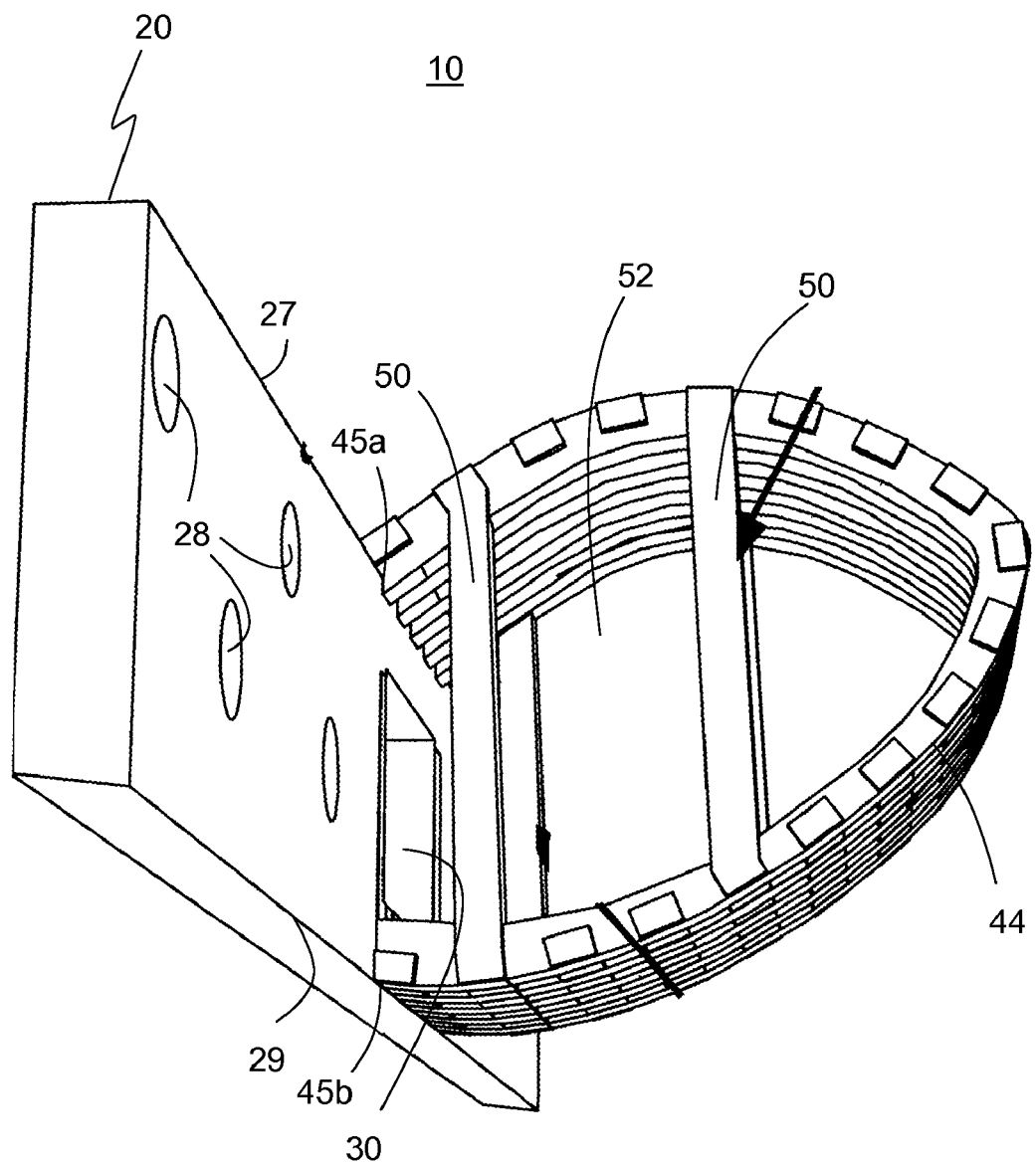
FIG. 4 is a perspective top view of the embodiment in FIG. 1 showing the inside of the tubularly-shaped containment cage.

Turning now to FIG. 4, there is illustrated a perspective top view of the present invention. As can be seen, tubularly-shaped containment cage 40 has an internal space or cage volume 52 formed by circumferential cage wall 41. Cage braces 50 disposed at cage ends 48, 48' are more clearly shown. As previously disclosed, an osteogenic material may optionally be disposed in internal space 52 either before or after placement of bone loss plate 10. The mesh wall structure allows bone growth to penetrate containment cage 40 during the healing process.

Bone loss plate 10 is used to treat bone pathology where a significant portion of bone is lost. The bone requiring treatment can be envisioned to have two ends, one proximal and one distal, and a gap of unspecified length between the two opposing ends. Tubularly-shaped containment cage 40 of bone loss plate 10, being approximately concentric with the cross-sectional shape of the bone ends, is placed in the gap in the bone so that the opposing ends of the bone will be in contact and supported by the cage ends 48, 48' of containment cage 40 and optional cage braces 50. Containment cage 40 may be filled with osteogenic material before or after positioning. When containment cage 40 is properly positioned in the gap, fixation plate 20 will lay flat along the length of the respective shafts of the pathologic bone. Fixation plate 20 is then fastened to the bone shafts by screws that are placed through fastener openings 28 in fixation plate 20.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A bone loss plate for the rigid fixation of a long bone having a bone gap where portions of the bone are absent, the plate comprising:

an elongated fixation plate having a cage aperture located in a middle portion of the fixation plate, a first end for fixation to the long bone on one side of the bone gap, a second end for fixation to the long bone on the opposite side of the bone gap; and a tubularly-shaped containment cage forming a circumferential cage wall with a first open end, a second open end and a plurality of cage wall openings, the circumferential cage wall connected to the middle portion of the fixation plate wherein the cage aperture of the fixation plate communicates with an interior of the containment cage to permit the addition of osteogenic bone material to the interior of the containment cage after the containment cage of the bone loss plate is positioned within the bone gap of a bone and the fixation plate is secured to the bone having the bone gap, the containment cage having the first and second open ends shaped similar to the cross-sectional shape of the long bone at the bone gap wherein the tubularly-shaped containment cage is expandable along a longitudinal axis that is parallel to a longitudinal axis of the fixation plate.

2. The plate of claim 1 wherein the long bone is selected from the group consisting of a tibia, a femur, a fibula, a humerus, a radius, and an ulna.

3. The plate of claim 1 wherein the circumferential cage wall has one or more cage braces extending across one of the first open end, the second open end or both of the tubularly-shaped containment cage.

* * * * *